United States Patent
Ohl et al.

(10) Patent No.: US 10,966,624 B2
(45) Date of Patent: Apr. 6, 2021

(54) MICROELECTRODE ARRAY FOR AN ELECTROCORTICOGRAM

(71) Applicants: Leibniz-Institut Für Neurobiologie, Magdeburg (DE); Otto-Von-Guericke-Universität, Magdeburg (DE)

(72) Inventors: Frank Ohl, Osterweddingen (DE); Michael Lippert, Leipzig (DE); Sören Hirsch, Wusterwitz (DE); Bertram Schmidt, Villingen-Schwenningen (DE); Martin Deckert, Magdeburg (DE)

(73) Assignees: Leibniz-Institut Für Neurobiologie, Magdeburg (DE); Otto-Von-Guericke-Universität, Magdeburg (DE)

( * ) Notice: Subject to any disclaimer, the term of this patent is extended or adjusted under 35 U.S.C. 154(b) by 100 days.

(21) Appl. No.: 16/185,053

(22) Filed: Nov. 9, 2018

(65) Prior Publication Data
US 2019/0192032 A1 Jun. 27, 2019

Related U.S. Application Data

(63) Continuation of application No. 14/439,810, filed as application No. PCT/EP2013/072638 on Oct. 29, 2013, now abandoned.

(30) Foreign Application Priority Data

Oct. 30, 2012 (DE) ...................... 10 2012 110 358.5

(51) Int. Cl.
*A61B 5/0478* (2006.01)
*A61N 1/05* (2006.01)
(Continued)

(52) U.S. Cl.
CPC .......... *A61B 5/0478* (2013.01); *A61B 5/0084* (2013.01); *A61B 5/01* (2013.01);
(Continued)

(58) Field of Classification Search
CPC ....... A61B 5/0084; A61B 5/01; A61B 5/0478; A61B 5/0484; A61B 5/0529; A61B 5/0601; A61B 5/0622; A61B 5/04001
See application file for complete search history.

(56) References Cited

U.S. PATENT DOCUMENTS 7,729,773 B2   6/2010  Sloan
8,886,334 B2 * 11/2014  Ghaffari .................. A61B 5/00
                                                                    607/115
(Continued)

FOREIGN PATENT DOCUMENTS

DE   10 2009 051 276    5/2011
DE   10 2010 019 597   11/2011
(Continued)

OTHER PUBLICATIONS

International Search Report and Written Opinion dated Mar. 27, 2014 corresponding to application No. PCT/EP2013/072638 filed on Oct. 29, 2013.
(Continued)

*Primary Examiner* — Christopher A Flory
(74) *Attorney, Agent, or Firm* — Renner, Otto, Boisselle & Sklar, LLP

(57) ABSTRACT

The invention relates to a method for obtaining brain wave data using a microelectrode array, comprising a plurality of electrodes for electrically measuring brain waves and an integrated optical stimulation unit for stimulating brain regions by means of optical signals, wherein the stimulation unit has one or more electrical light sources, and wherein the method includes stimulating neurons of the brain via optical
(Continued)

signals produced by the light sources, recording a response of the neurons to the stimulation via the electrodes, unambiguously assigning the recorded response to individual optical stimulation signals provided by the light source, and determining an unambiguous correlation between the optical stimulation signals and resulting brain waves measured by the electrodes.

18 Claims, 5 Drawing Sheets

(51) Int. Cl.
*A61N 5/06* (2006.01)
*A61B 5/00* (2006.01)
*A61B 5/01* (2006.01)
*A61B 5/0484* (2006.01)
*A61B 5/04* (2006.01)
*G06T 5/50* (2006.01)
*H04N 5/235* (2006.01)
*H04N 5/355* (2011.01)

(52) U.S. Cl.
CPC .......... *A61B 5/0484* (2013.01); *A61N 1/0529* (2013.01); *A61N 5/0601* (2013.01); *A61N 5/0622* (2013.01); *G06T 5/50* (2013.01); *H04N 5/2355* (2013.01); *H04N 5/35554* (2013.01); *A61B 5/04001* (2013.01); *A61B 5/686* (2013.01); *A61B 5/6849* (2013.01); *A61B 5/6868* (2013.01); *A61B 2562/028* (2013.01); *A61B 2562/0209* (2013.01); *A61N 2005/0652* (2013.01); *A61N 2005/0653* (2013.01); *G06T 2207/10144* (2013.01); *G06T 2207/20221* (2013.01)

(56) References Cited

U.S. PATENT DOCUMENTS

| | | | |
|---|---|---|---|
| 8,934,965 B2* | 1/2015 | Rogers | A61F 2/72 600/544 |
| 9,159,635 B2* | 10/2015 | Elolampi | H05K 3/4644 |
| 9,171,794 B2* | 10/2015 | Rafferty | H01L 24/06 |
| 9,289,132 B2* | 3/2016 | Ghaffari | A61B 5/01 |
| 9,450,043 B2* | 9/2016 | Nuzzo | H01L 33/32 |
| 9,521,955 B2* | 12/2016 | Ma | A61B 5/4076 |
| 9,554,484 B2* | 1/2017 | Rogers | A61B 5/01 |
| 2004/0082862 A1* | 4/2004 | Chance | A61B 5/4064 600/473 |
| 2007/0060984 A1* | 3/2007 | Webb | A61N 5/0622 607/89 |
| 2007/0100398 A1* | 5/2007 | Sloan | A61N 1/36071 607/62 |
| 2008/0288037 A1* | 11/2008 | Neysmith | A61N 1/0543 607/116 |
| 2009/0054955 A1* | 2/2009 | Kopell | A61N 5/0601 607/88 |
| 2010/0241006 A1* | 9/2010 | Choi | A61B 5/0084 600/476 |
| 2011/0021885 A1* | 1/2011 | Ma | A61B 5/4076 600/301 |
| 2011/0034912 A1* | 2/2011 | de Graff | H01L 27/14618 606/21 |
| 2011/0125077 A1* | 5/2011 | Denison | A61N 5/0622 604/20 |
| 2011/0208675 A1* | 8/2011 | Shoureshi | G05B 13/0285 706/2 |
| 2011/0230747 A1* | 9/2011 | Rogers | A61B 5/05 600/377 |
| 2011/0237921 A1* | 9/2011 | Askin, III | A61B 5/0478 600/377 |
| 2012/0032147 A1* | 2/2012 | Nagai | H01L 27/1446 257/21 |
| 2012/0123508 A1* | 5/2012 | Wentz | A61N 5/0601 607/88 |
| 2012/0253261 A1* | 10/2012 | Poletto | A61N 5/0601 604/20 |
| 2013/0041235 A1* | 2/2013 | Rogers | A61B 5/1107 600/306 |
| 2013/0140649 A1* | 6/2013 | Rogers | H01L 29/66007 257/414 |
| 2014/0163390 A1* | 6/2014 | Rogers | A61L 31/148 600/476 |

FOREIGN PATENT DOCUMENTS

| | | |
|---|---|---|
| DE | 10 2012 002 663 | 8/2013 |
| WO | 2010/025226 | 3/2010 |

OTHER PUBLICATIONS

Esther Krook-Magnuson et al., Neuroelectronics and Biooptics, Closed-Loop Technologies in Neurological Disorders, Jul. 2015.

* cited by examiner

MICROELECTRODE ARRAY FOR AN ELECTROCORTICOGRAM

RELATED APPLICATIONS

This application is a continuation of U.S. application Ser. No. 14/439,810, which was filed Apr. 30, 2015, which is a national phase of International Application No. PCT/EP2013/072638 filed Oct. 29, 2013 and published in the German language, which claims priority to German Application No. 10 2012 110 358.5 filed Oct. 30, 2012.

The invention relates to a microelectrode array comprising a multiplicity of electrodes for electrically measuring brain waves as claimed in claim 1.

There are already approaches for miniaturizing electrodes for measuring brain waves in particular in the form of so-called microelectrode arrays. In this case, the term array denotes an arrangement of a multiplicity of electrodes which can be arranged regularly or irregularly, e.g. in a matrix arrangement. Such electrodes or such microelectrode arrays can be used to record electrical signals of the brain of a living being, measurements being possible both on the brain surface and within the brain. In particular, an electrocorticogram (ECoG), can be recorded using such microelectrode arrays.

Moreover, there are developments in the field of so-called "optogenetics", involving the use of light to stimulate neurons in the brain, provided that they express specific light-sensitive channel proteins. The light required for the stimulation is typically radiated into the brain from outside through optical fibers or light emitting diodes (LEDs) mounted on the skull.

A number of problems arise here, namely that the implantation of the light source and of the microelectrode array takes up a great deal of room spatially, the experimental objects are linked to external technology by means of an optical waveguide and the exact spatial alignment of the light source and the individual electrodes with respect to one another is difficult. The entire implantation process is relatively complicated owing to the need for a plurality of steps and technologies.

The invention is based on the object of simplifying this.

The object is achieved as claimed in claim 1 by means of a microelectrode array comprising a multiplicity of electrodes for electrically measuring brain waves and comprising an integrated optical stimulation unit for stimulating brain regions with optical signals, wherein the stimulation unit has one or a plurality of electrical light sources. One advantage of the invention is that the electrical light source or the electrical light sources is/are integrated into the microelectrode array and therefore need not be positioned and implanted as separate parts. The electrical contacting is also simplified since common lines, e.g. in the form of a ribbon cable, can be used. A further advantage of the invention is that the electrical light source or the electrical light sources is/are spatially fixed and exactly positioned in relation to the electrodes, wherein the exact positioning is already predefined by the production of the microelectrode array. Therefore, the microelectrode array according to the invention is significantly more application-friendly than known devices. The invention makes it possible for cortical neurons to be optically stimulated spatially precisely and in a structured fashion with the aid of one or a plurality of integrated electrical light sources and at the same time for the thereby triggered and spontaneous brain waves to be derived electrophysiologically through the microstructured electrodes.

A further advantage is that there is the possibility of stimulating brain regions with different spatial patterns, for example in order to measure and stimulate topographical relations in the brain, e.g. for tonotopy, somatotopy, retinotopy.

In accordance with one advantageous development of the invention, the microelectrode array has a filmlike, thin substrate. The substrate can be a flexible substrate, in particular. Suitable materials for producing the substrate are e.g. films composed of polyimide, parylene, polydimethylsiloxane (PDMS) or polyurethane. It is advantageous, in particular, to use an optically sufficiently transparent material, e.g. a film material, for the substrate, such that the light emitted by the electrical light sources can penetrate through the substrate. The substrate can be constructed from the same or different materials in particular in a multilayered fashion, e.g. in the manner of a sandwich structure.

In accordance with one advantageous development of the invention, the electrodes are arranged in a manner distributed over the areal extent of the substrate on the surface of the substrate or in the substrate. The electrodes can be embodied e.g. as electrically conductive coating, e.g. as metal coating, on the surface of the substrate or as metal layer in the substrate. In accordance with one advantageous development of the invention, a multiplicity of electrical light sources of the stimulation unit are arranged in a manner distributed over the areal extent of the substrate on the surface of the substrate or in the substrate.

The electrical light sources can be embodied in particular as light emitting diodes, wherein inorganic light emitting diodes or organic light emitting diodes (OLEDs) can be employed, including in combination with one another. Furthermore, the electrical light source or the electrical light sources can be integrated into the construction of the microelectrode array as phosphorescent organic light emitting diodes (PHOLEDs) or can be used in combination with the abovementioned light sources. The improved efficiency of the PHOLEDs in comparison with other light sources is advantageous since, for the same light intensity, a reduced evolution of heat is induced and the risk of tissue damage or damage to brain regions as a result of heating is reduced.

In accordance with one advantageous development of the invention, it is provided that the electrical light source or the electrical light sources is/are arranged according to a fixed, predefined scheme relative to the electrodes and is/are distributed over the areal extent of the substrate. A fixedly predefined assignment between the electrodes and the electrical light sources is predefined as a result, such that the stimulation—recorded via the electrodes—of the neurons by means of the electrical light sources can be unambiguously assigned in individual stimulation signals, such that an unambiguous correlation can be determined.

In accordance with one advantageous development of the invention, electrically conductive structures are formed on the surface of the substrate or in the substrate, said electrically conductive structures forming the electrodes, electrical connection lines to the electrodes and/or electrical connection lines to the electrical light source or the electrical light sources. This has the advantage that the electrically conductive structures, e.g. in the form of one or a plurality of metal layers, can be directly embedded in the substrate or can be applied thereto, e.g. can be applied by vapor deposition.

The electrically conductive structures can be provided e.g. in the form of one or a plurality of metallization planes in the substrate. The metallization plane or the metallization planes forming the electrodes and/or connection lines can be used directly for the power supply of the light sources. An additional, if appropriate thicker and/or structured metal layer can also be provided for the purpose of power supply in the microelectrode array.

In accordance with one advantageous development of the invention, the microelectrode array has a sensor side, which is designed to be brought into contact with the brain surface of a living being to be examined. In this case, one, a plurality or all of the electrical light sources can advantageously be arranged at a greater distance from the sensor side than the electrodes. This enables the light sources to be accommodated expediently. In particular, it is possible to arrange one, a plurality or all of the electrical light sources on that surface of the substrate which faces away from the sensor side. Furthermore, the advantageous arrangement of the electrical light source or of the electrical light sources at a relative distance from the sensor side makes it possible to reduce the heat input into the stimulated brain regions, in order to prevent tissue damage.

The electrical light sources can be arranged in particular as SMD components, as dies or as thin-film elements on the substrate or within the substrate.

In accordance with one advantageous development of the invention, at least the sensor side of the microelectrode array is electrically and biologically passivated. Undesirable reciprocal effects with the brain tissue are avoided as a result. The passivation can be embodied e.g. as insulation layer.

In accordance with one advantageous development of the invention, the electrodes are integrated into the material of the substrate, e.g. embedded therein. The substrate then has, on a sensor side designed to be brought into contact with the brain surface of a living being to be examined, openings leading to the electrodes. As a result, the electrical contact to the electrodes can be produced even with electrodes integrated into the material of the substrate. The integration of the electrodes into the substrate has the advantage that they are arranged in a space-saving fashion therein and are better protected against damage.

In accordance with one advantageous development of the invention, one, a plurality or all of the electrodes is/are embodied as ECoG electrodes.

In accordance with one advantageous development of the invention, the microelectrode array has one or a plurality of stimulation electrodes for stimulating brain regions with electrical signals. This has the advantage that a stimulation is additionally possible by means of electrical signals that are transferred to brain regions directly galvanically. The microelectrode array can thus also carry out combined stimulations with optical and electrical signals. The application possibilities for the microelectrode array are extended as a result.

In accordance with one advantageous development of the invention, one or a plurality of electrodes for electrically measuring brain waves is/are simultaneously stimulation electrodes for stimulating brain regions with electrical signals. In this case, one advantage is that the microelectrode array can be embodied with a multiplicity of electrodes and the latter are optionally used as measuring electrodes or as stimulation electrodes. In accordance with one advantageous development of the invention, electrodes are used at times for electrically measuring brain waves and at times as stimulation electrodes for stimulating brain regions with electrical signals. The function of the respective electrode can be correspondingly controlled by means of control electronics.

In accordance with one advantageous development of the invention, in each case one or a plurality of further electrical and/or electronic components, in particular sensor components, is/are arranged in relative proximity to one, a plurality or all of the electrical light sources. This has the advantage that, by means of the further electrical and/or electronic component(s), depending on the embodiment thereof, further possibilities for influencing the tissue or brain regions are possible or, if sensor components are involved, further data can be acquired. In this regard, a further electrical and/or electronic component or a group of such components can be assigned in each case to an electrical light source and be arranged in proximity thereto, e.g. alongside the light source or in a manner distributed around the light source.

In accordance with one advantageous development of the invention, in each case one or a plurality of further electrical and/or electronic sensor components, each of which outputs an electrical sensor signal, is/are arranged in relative proximity to one, a plurality or all of the electrical light sources in such a way that at least one physical variables influenced by the electrical light source or the electrical light sources are detectable by the respective sensor component. This has the advantage that such sensor components can monitor physical variables influenced by the light sources such as e.g. the light which is emitted by the respective light source and which can be detected directly on site, if appropriate taking account of reflection and/or absorption properties of the brain tissue. Other physical variables influenced by the electrical light sources such as e.g. the local temperature, can also be detected. The data detected by the sensor components can be displayed on a display unit, for example, and thus be monitored visually. Automatic monitoring for compliance with permissible limit values can also be carried out, e.g. in such a way that, in the event of specific limit values being exceeded or undershot, an indication signal to the user is generated automatically. Moreover, it is advantageously possible to use the detected sensor signals in turn for influencing the light sources or the light emitted thereby, such that the light sources can be controlled depending on the sensor signals. It is also possible to realize a complete regulating circuit for regulating the electrical light sources depending on sensor signals of the electrical and/or electronic sensor components. In this case, the light sources can be controlled and/or regulated e.g. by variation of electrical parameters such as current and/or voltage. The electrical parameters can also be influenced by means of pulsed signals, the duty ratio of which is varied.

In accordance with one advantageous development of the invention, one, a plurality or all of the electrical light sources have one or a plurality of sensor components assigned to the respective light source, each of which sensor components outputs an electrical sensor signal which is assignable to the influenced physical variable of a specific light source. Such a possibility of assigning the physical variable influenced by the light source to the light source makes it possible to carry out an independent, differentiated control and/or regulation of the respective individual light source in a targeted manner, which is advantageous particularly in the case of a large number of electrical light sources.

In accordance with one advantageous development of the invention, one, a plurality or all of the sensor components is/are embodied as temperature sensors. This has the advantage that the local temperature in the tissue or in brain regions can be measured. In particular, it is possible to carry out a measurement of the temperature increase brought about by the light source or the light sources in the tissue or in the brain regions. In conjunction with the abovementioned control and/or regulation of the light source, it can be ensured that the temperature increase caused by the light sources is kept within limits such that damage to the tissue is avoided. The temperature increase can thus be restricted to permissible limit values by means of regulation technology.

Heating of stimulation electrodes, e.g. caused by the light sources, can also be detected by means of such temperature sensors.

Such temperature sensors can be embodied as meanders, for example, and the temperature dependence of the electrical resistance of the metallization can be utilized as measurement principle. The temperature sensors can be produced from platinum, for example, wherein the electrodes of the microelectrode array can also be produced from platinum. Other embodiments of temperature sensors are also usable.

The advantage of the integration of temperature sensors is based on the temperature measurements simultaneously with the stimulation of brain regions with optical signals in relative proximity to the electrical light source or the electrical light sources, in order to monitor and/or prevent the risk of tissue damage or damage to brain regions as a result of impermissible heating.

In accordance with one advantageous development of the invention, one, a plurality or all of the sensor components is/are embodied as light-sensitive sensors. In principle, all known types of light-sensitive sensors can be used for this purpose, such as e.g. light-sensitive resistors or photodiodes. Inorganic and/or organic photodiodes are particularly advantageous since they are readily integratable into the microelectrode array. The use of such light-sensitive sensors as further sensor components of the microelectrode array has the advantage that a simultaneous measurement of the light intensity of the stimulating optical signals becomes possible, which enables the correlation of the light intensity applied for stimulating cortical neurons or the brain regions with the neuronal activity recorded via the electrodes. Corresponding computer-aided evaluation of the signals of the electrodes and the signals of the light-sensitive sensors makes it possible to determine corrected electrode signals from which undesirable side effects such as e.g. shadings of light sources or reflections of the emitted light have been eliminated. At the same time, it is possible to determine the absorption and the scattering of the stimulating optical signals by cortical tissue. In conjunction with the abovementioned control and/or regulation of the electrical light sources depending on the sensor signals, it is also possible to carry out an automatic correcting function of the light emission of the light sources to desired light emission values by means of the sensor signals being checked to ascertain whether the desired light emission values of the light sources are achieved and, if this is not the case, a corrective intervention being carried out by control and/or regulation of the electrical light sources.

The above-mentioned control and/or regulation functions can advantageously be realized by an electronic control unit which carries out the control and/or regulation functions in terms of hardware and/or by software control, e.g. using a microprocessor or microcontroller.

In accordance with one advantageous development of the invention, the further electrical and/or electronic components are arranged according to a fixed, predefined scheme relative to the light sources and are arranged in a manner distributed over the areal extent of the substrate on the surface of the substrate or in the substrate. This enables e.g. an area-covering sensor-based detection of variables over the entire microelectrode array.

In accordance with one advantageous development of the invention, electrically conductive structures are formed on the surface of the substrate or in the substrate, said electrically conductive structures forming electrical connection lines to the further electrical and/or electronic component or to the further electrical and/or electronic components. In this way, e.g. the temperature sensors and/or the light-sensitive sensors can be electrically contacted without external lines. The electrical connection lines can be realized e.g. in the same way as in the case of the electrical light sources.

Direct embedding of electrical connection lines in the substrate can be carried out e.g. by deposition of metallic materials e.g. by cathode sputtering. Such embedding of the electrical connection lines on the substrate increases the degree of integration and thus allows an extended functionality of the microelectrode array, e.g. for temperature measurement and measurement of the light intensity, without structural enlargement.

The electrically conductive structures, embodied e.g. as metallization planes, can thus be used e.g. directly for the power supply of the temperature sensor or of the temperature sensors and/or of the light-sensitive sensor or of the light-sensitive sensors. It is advantageous here for the number of function-integrating metallization planes not to be chosen to be excessively large, e.g. for only one metallization plane to be used. As a result, it is possible to improve the achievable mechanical flexibility with low stiffness of the microelectrode array, whereby an improved adaptability of the microelectrode array to the topography of the brain surface is made possible at the same time.

In accordance with one advantageous development of the invention, one, a plurality or all of the further electrical and/or electronic components are arranged as SMD components, as dies or as thin-film elements on the substrate or within the substrate. This has the advantage that the electrical and/or electronic components are arranged in a space-saving fashion on or in the substrate and can be better protected against damage. Bringing one, a plurality or all of the electrical and/or electronic components, in particular the sensor components such as the temperature sensors, near to the sensor side in the substrate allows the detection of physical variables, in particular a temperature measurement, which has a high degree of correlation with actual physical variables of stimulated brain region.

In accordance with one advantageous development of the invention, the microelectrode array has a receiving apparatus for wirelessly receiving electromagnetic waves emitted onto the microelectrode array. The microelectrode array is wirelessly suppliable with the electrical energy required for its operation via the receiving apparatus and/or a rechargeable battery of the microelectrode array is wirelessly chargeable via the receiving apparatus. The receiving apparatus can be embodied e.g. as a coil which is provided on the substrate or within the substrate and which is formed e.g. from the material of the electrically conductive structures from which the already mentioned electrical connection lines to the light sources or the other electrical and/or electronic components can be formed. This has the advantage that there is no need for any cable connection for supplying the microelectrode array with electrical energy. Instead, e.g. an energy transmitting coil embedded into a flexible mat can be placed externally onto the skin surface or the hair of a patient and the microelectrode array can be wirelessly supplied with electrical energy by said coil by means of a radio-frequency signal via the receiving apparatus. A rechargeable battery possibly present in the microelectrode array can also be charged thereby. By way of example, provision can be made of a rechargeable battery of the lithium polymer type in the form of a flat layer in the microelectrode array.

In accordance with one advantageous development of the invention, the microelectrode array has a wirelessly operating signal transfer device designed for wirelessly transferring signals, in particular in the form of data, from the microelectrode array to a signal receiving device and/or for wirelessly transferring signals, in particular in the form of data, from a signal transmitting device to the microelectrode array. This has the advantage that there is no need for any cable connections for the signal transfer and/or the data transfer. The signal transfer device can be designed e.g. according to one of the known standards, e.g. as a Bluetooth signal transfer device. The use of such cable-free connections allows the reduction of the risk of inflammation after the microelectrode array has been implanted. The advantage is based on the omission of cable feedthroughs, such as e.g. ribbon cables, through the scalp. In particular, the risk of infection can also be reduced as a result. The required electronic components, e.g. amplifiers, impedance converters, filters, multiplexers, analog/digital converters, energy stores, can be wholly or partly combined e.g. in an application specific integrated circuit (ASIC).

In accordance with one advantageous development of the invention one, a plurality or all of the electrodes is/are integrated in a respectively elevated column structure which spaces apart the individual electrodes on the sensor side from the substrate plane. This has the advantage that the electrodes on the sensor side can project somewhat from the substrate and can thus be led better or with greater sealing to positions to be sensed on the brain surface. Furthermore, it is thereby possible to increase the distance between the electrical light sources and the brain surface, such that the heat input into the brain surface is reduced. The microtechnological fabrication of the column structures can implement e.g. lithographic masking and wet-chemical patterning of a metallic hard mask, wherein the structure transfer to the substrate is realized with the aid of a dry etching process, for example. The use of a thicker substrate film and/or the progressive deposition of a plurality of substrate thin-film layers allows the production of column structures having varying dimensions. Capillary blood vessels and biological structures on the brain surface which impose limits on bringing planar microelectrode arrays near to the brain surface can be overcome by such elevated column structures. In this case, the flexible substrate material allows local bypassing of biological structures. The advantage of such electrode structures is accordingly based on bringing the electrodes near to the brain surface without penetrating the latter, and results in an improved spatial resolution of derivation and stimulation. A further advantage is that the three-dimensional column structures prevent implanted microelectrode arrays from slipping.

In accordance with one advantageous development of the invention, one, a plurality or all of the column structures is/are produced from the substrate material. This allows an efficient production process for the microelectrode array. Furthermore, biological compatibility is still afforded since no further materials are required.

In accordance with one advantageous development of the invention, one, a plurality or all of the column structures has/have a respectively circumferential sealing lip which laterally delimits the active electrode area of the electrode integrated into the column structure. In this case, the substrate can in turn have on the sensor side openings which lead to the electrodes and which expose the active electrode areas. The circumferential sealing lips separate the electrode areas from the surrounding cerebrospinal fluid, prevent compensation currents between the electrodes and produce the direct contact with the brain surface. This ensures the highest possible spatial resolution and best signal-to-noise ratios of such non-penetrating microelectrode arrays.

In accordance with one advantageous development of the invention, through openings are arranged in the substrate of the microelectrode array, said through openings being suitable for allowing the diffusion of pharmacological substances into the tissue and/or for introducing one or a plurality of penetrating depth electrodes into the tissue. The through openings are advantageously arranged at positions at which the electrodes, the electrical light sources or the other electrical and/or electronic components of the microelectrode array are precisely not arranged. In this regard, the through openings can be arranged e.g. in proximity to the electrodes, the electrical light source or the electrical light sources, the further electrical and/or electronic component or components in the substrate. The through openings allow e.g. pharmacological substances e.g. for optogenetic applications to be introduced into the tissue. One or a plurality of penetrating depth electrodes can also be introduced into the cortical tissue. The application possibilities of the microelectrode array are fundamentally extended as a result. At the same time, the through openings bring about capillary effects that advantageously influence the suction of the microelectrode array to the brain surface and the displacement of surrounding cerebrospinal fluid.

In accordance with one advantageous development of the invention, a plurality or all of the through openings are arranged in a manner distributed over the areal extent of the substrate according to a fixed, predefined pattern.

In accordance with one advantageous development of the invention, one or a plurality of depth electrodes or at least one depth electrode array for simultaneously electrically measuring brain waves of deeper brain regions and/or electrically and optically stimulating deeper brain regions is/are inserted into the through openings. A depth electrode array is understood to mean an arrangement of depth electrodes which are arranged on a common carrier at fixed positions with respect to one another. The application possibilities of the microelectrode array are fundamentally extended as a result. This has the advantage that the signal space can be enlarged on account of the depth information and it is possible to ascertain corresponding correlations in derivation and stimulation.

The object mentioned in the introduction is furthermore achieved by means of a device comprising a microelectrode array of the type explained above and at least one electronic control device, wherein the electronic control device is coupled to one, a plurality or all of the electrical and/or electronic components of the microelectrode array. In particular, the electronic control device can be coupled to the electrodes of the microelectrode array, the electrical light sources, further electrical and/or electronic components and/or the depth electrodes. The electronic control device can be wholly or partly integrated into the microelectrode array. On account of the structural size of present-day electronic control devices, it is advantageous to realize at least part of the electronic control device separately from the microelectrode array, e.g. in a separate control unit which picks up and evaluates the signals output by the microelectrode array and, if appropriate, outputs control signals to the electrical light sources. The control of the electrodes depending on sensor signals of the microelectrode array, e.g. in the context of the regulating circuit mentioned, can be realized locally on the microelectrode array by means of a part of the electronic control device integrated there, or externally to the microelectrode array in the separate control unit.

The electronic control device can be coupled to one, a plurality or all of the electrical and/or electronic components of the microelectrode array in a wired fashion and/or wirelessly. Wireless coupling has the advantage that the microelectrode array is handleable more easily after it has been implanted, and there is a reduced burden on the patient.

In accordance with one advantageous development of the invention, the electronic control device is coupled at least to one, a plurality or all of the electrical light sources and is designed for controlling the light emission from one, a plurality or all of the coupled electrical light sources.

Furthermore, it can be provided that the electronic control device is designed for controlling the light emission from one, a plurality or all of the coupled electrical light sources depending on electrical and/or electronic sensor components of the microelectrode array, each of which an electrical sensor signal depending on at least one physical variable which is influenced by the electrical light source or the electrical light sources and which is detected by the respective sensor component.

The microelectrode array and the device comprising a microelectrode array can be used e.g. for mapping brain functions and/or for analyzing epileptogenic zones. An application as the human-machine interface (HMI) or brain-machine interface (BMI) is also advantageous.

The invention is explained in greater detail below on the basis of exemplary embodiments using drawings.

In the figures.

In the figures, identical reference signs are used for mutually corresponding elements.

Figure 1:
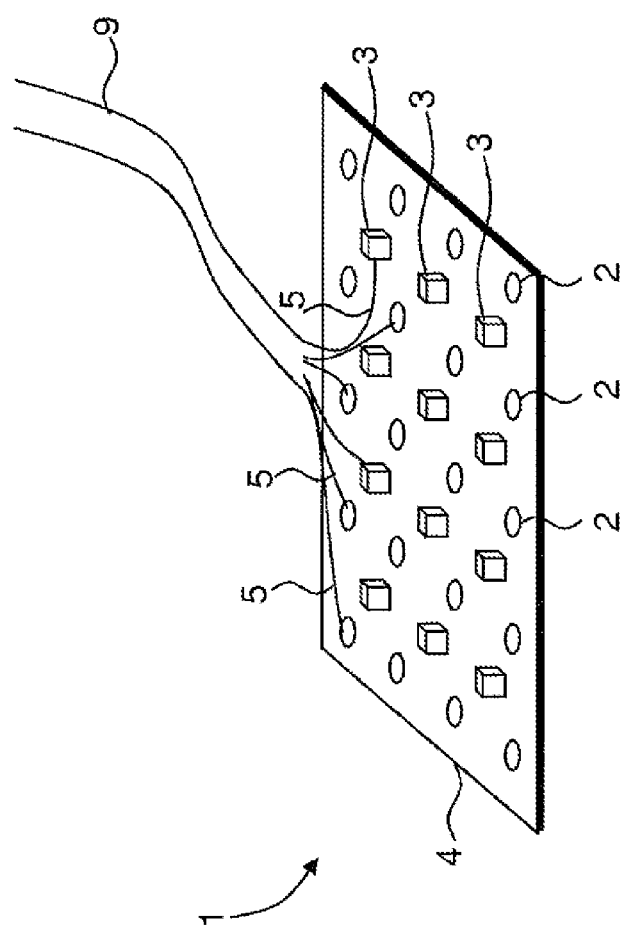
FIG. 1 shows a microelectrode array in an isometric illustration.

FIG. 1 shows a microelectrode array 1, which can be embodied e.g. as a thin-film array comprising a flexible, filmlike thin substrate 4. A plurality of electrodes 2, each represented by circles, and a plurality of electrical light sources 3 in the form of light emitting diodes, each represented in the form of squares, are arranged on or in the substrate 4. The electrodes 2 and the light emitting diodes 3 are connected to a connection cable 9 via electrical lines 5, of which only a few lines are illustrated by way of example for reasons of clarity in FIG. 1. The connection cable 9 can be embodied e.g. as a ribbon cable. Via the connection cable 9, the electrical signals of the electrodes 2 are conducted to an amplifier and a measuring system and the light emitting diodes 3 are additionally supplied with power.

The microelectrode array 1 can have dimensions in the millimeter or centimeter range with regard to width and length and can be embodied in different shapes, which can also deviate from the rectangular shape illustrated in FIG. 1.

Figure 2:
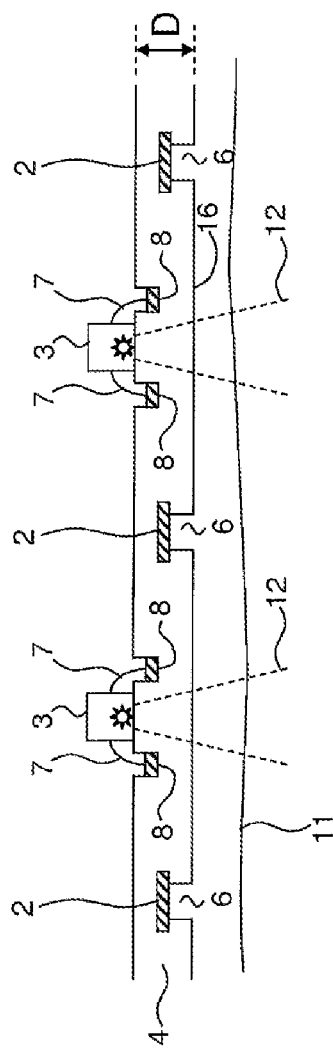
FIGS. 2, 3 and 5 show embodiments of a microelectrode array in lateral sectional illustration.

FIG. 2 shows one embodiment of the microelectrode array 1 in cross section. The thickness D of the substrate 4 is relatively small in comparison with the width and length. The thickness D can be in the micrometer range, in particular. The substrate 4 embodied as a thin, flexible film e.g. composed of parylene, polyimide, PDMS or polyurethane has metal structures 2, 8 introduced therein. The metal structures 2 form the electrodes 2 in substrate regions provided with openings 6. The openings 6 face a sensor side 16 of the substrate 4, said sensor side being designed to be brought into contact with the brain surface 11 of a living being to be examined. The metal structures 8 realize power supply lines of the light emitting diodes 3 that are separate from the electrodes 2, i.e. electrically isolated therefrom and are passivated with respect to the biological tissue or cortex 11. The light emitting diodes 3 are applied to the substrate 4 on that side of said substrate 4 which faces away from the brain surface 11, or are integrated into the substrate 4, e.g. in the manner of a sandwich structure. The light emitting diodes 3 are electrically connected to the power supply lines 8 either directly or by means of electrical connections 7, e.g. in the form of bonds. The light emitting diodes 3 emit their light 12 through the optically sufficiently transparent substrate 4 in the direction of the brain surface 11 and thereby stimulate the nerve cells present therein. The nerve cells can be made sensitive to light e.g. by means of channel rhodopsins. In this case, the path of the light 12 can also be influenced by the metal structures 2, 8 or by additional elements such as refractive or reflective optical elements, for example, which are present in the microelectrode array 1.

Figure 3:
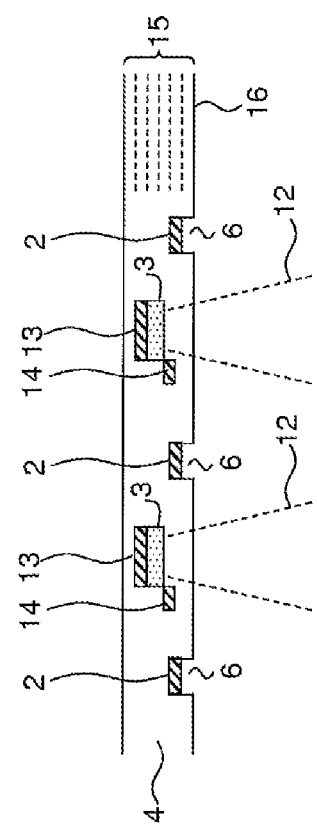

FIG. 3 shows a further embodiment of a microelectrode array in cross-sectional illustration. In accordance with FIG. 3, the light emitting diodes 3 are embodied in the form of thin-film LEDs integrated into the substrate 4, in particular as organic LEDs. In this case, the substrate 4 can advantageously be produced as a multilayer structure 15 composed of a plurality of layers. The light emitting diodes 3 are then introduced directly into the multilayer structure 15 of the substrate 4 in a microstructured fashion. They are contacted by metal layers 13, 14 in the multilayer structure 15 in order to ensure the power supply. The electrodes 2 are in turn open toward the sensor side 16 via openings 6. All other structures are electrically and biologically passivated.

Figure 4:
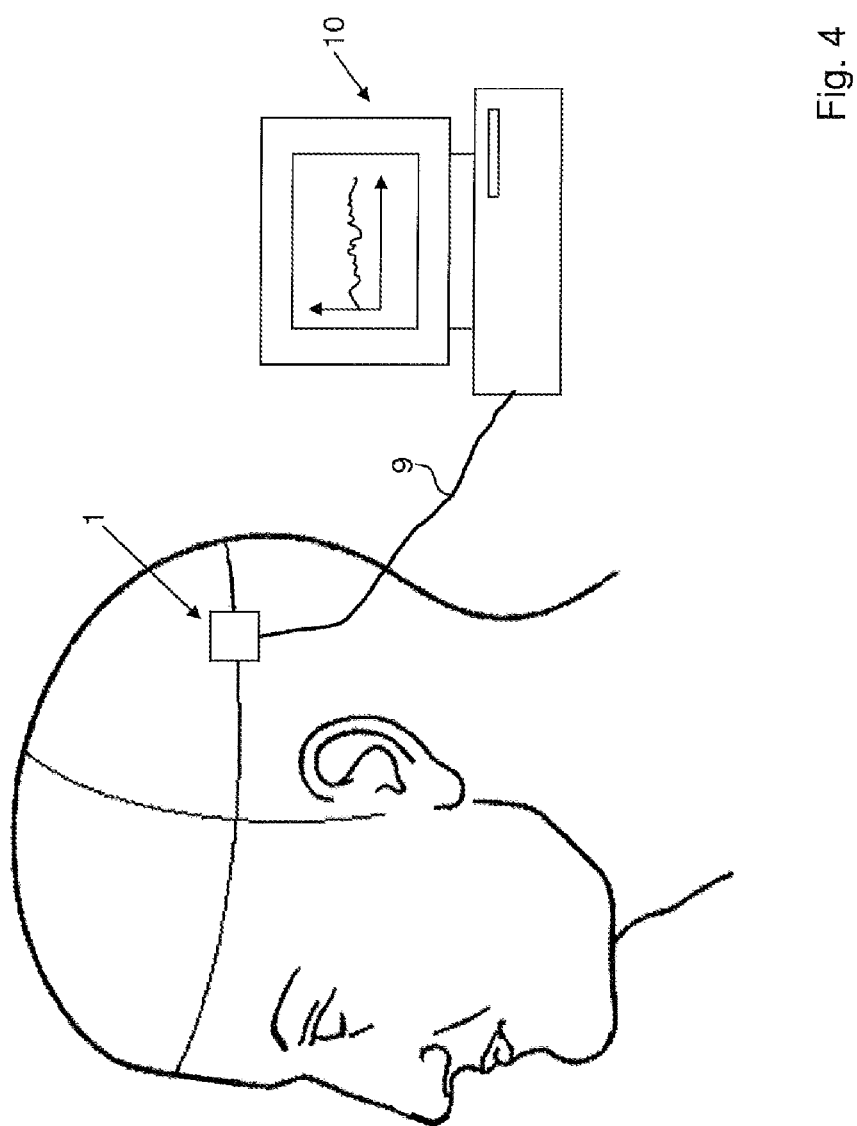
FIGS. 4 and 6 show the application of a microelectrode array when recording an electrocorticogram.

FIG. 4 shows an application of the microelectrode array 1 according to the invention when recording an electrocorticogram of a human being. The microelectrode array 1 is connected via the connection cable 9 to an electronic device 10, which comprises in particular an amplifier for the electrode signals and a data acquisition system. The recorded data can be displayed e.g. on a screen.

Figure 5:
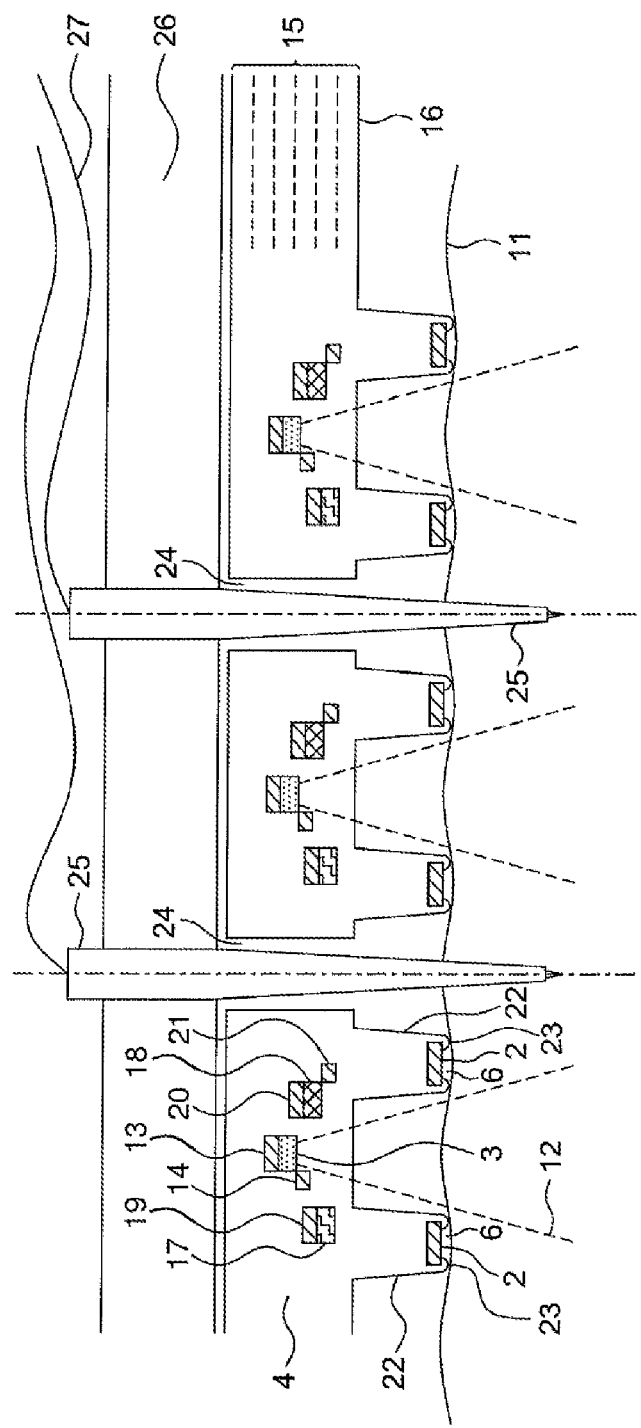

FIG. 5 shows a further embodiment of a microelectrode array in cross-sectional illustration. In accordance with FIG. 5, the electrodes 2 are embedded in elevated column structures 22, produced from the substrate material, for being brought near to the brain surface 11 and are in turn opened toward the sensor side 16 by openings 6. Microstructured, circumferential sealing lips 23 laterally delimit the active electrode areas of the electrodes 2. The light emitting diodes 3 are embodied in the form of thin-film LEDs integrated into the substrate 4, in particular as phosphorescent organic light emitting diodes, and are introduced directly into the multilayer structure 15 of the substrate 4 in a microstructured fashion. They are contacted by the metal structures 13, 14 in the multilayer structure 15 in order to ensure the power supply, and emit their light 12 through the optically sufficiently transparent substrate 4 in the direction of the brain surface 11. The metal structures 13, 14, 19, 20, 21 realize electrical connection lines that are separate from the electrodes 2, i.e. electrically isolated therefrom, and are passivated with respect to the biological tissue or cortex 11. In this case, the metal structures 19 form the power supply line of the temperature sensors 17, embodied as meanders for example, and the metal structures 20, 21 form the electrical contacting of the photodiodes 18. Temperatures sensors 17 and photodiodes 18 are embedded in the substrate, e.g. in the manner of a sandwich structure, and are thus electrically and biologically passivated. Through openings 24 are arranged in the substrate 4, said through openings being suitable for allowing the diffusion of pharmacological substances into the tissue for e.g. optogenetic applications, and/or for introducing penetrating depth electrodes 25 into the cortical tissue. The depth electrodes 25 are integrated in a positionally fixed manner at a defined distance in an adapted depth electrode array 26, wherein the cable-based electrical connection lines 27, embodied e.g. as ribbon cable, are led away on the side facing away from the sensor side 16.

FIG. 5 shows alongside one another three of the above-described arrangements in the substrate 4, which are constructed identically and therefore, only one arrangement of which has been completely provided with reference signs, for the sake of better clarity.

Figure 6:
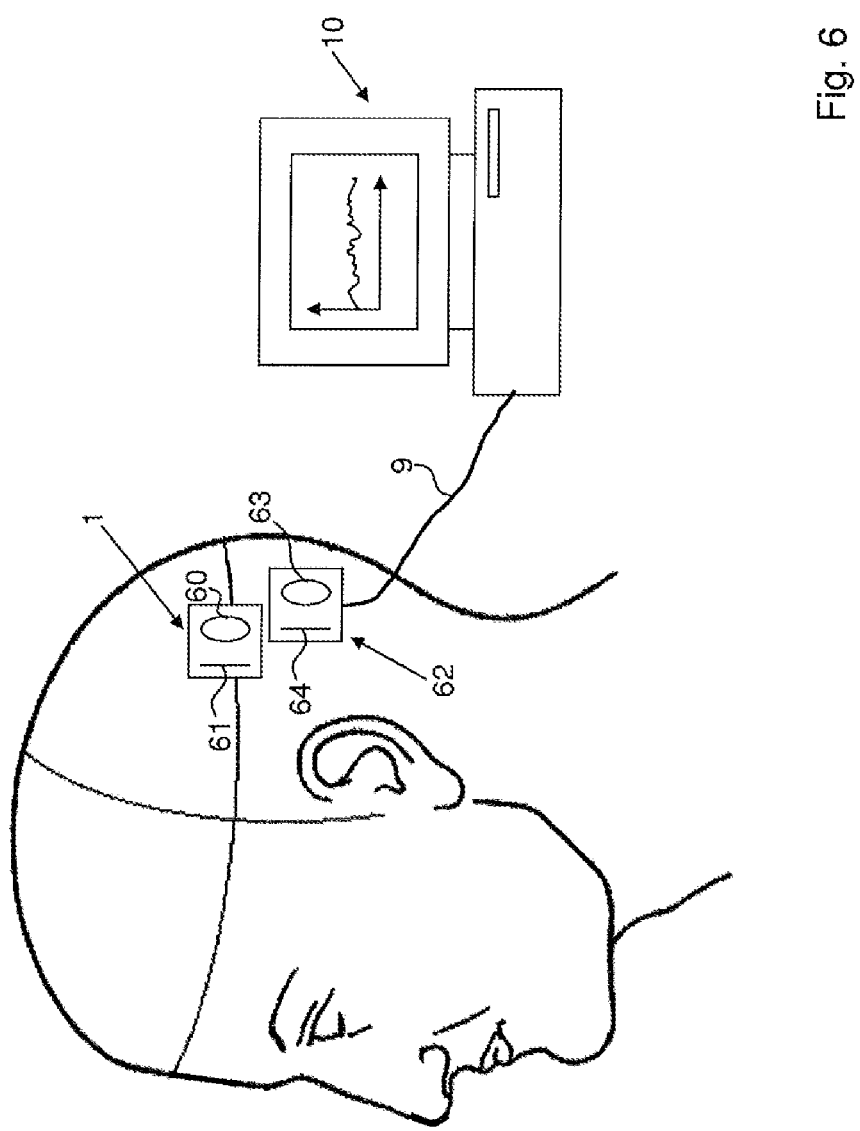

FIG. 6 shows an application of the microelectrode array 1 according to the invention when recording an electrocorticogram of a human being. In contrast to FIG. 4, the microelectrode array 1 is wirelessly connected to an electronic control device 10, which comprises in particular an amplifier for the electrode signals and a data acquisition system. The microelectrode array 1, implanted e.g. below the patient's scalp, has an energy receiving coil 60 and an antenna 61 for bidirectional data transfer between the microelectrode array 1 and the electronic control device 10. It is also possible for the energy receiving coil 60 simultaneously to be used as an antenna, such that no separate antenna 61 is required.

For this purpose, the electronic control device 10 is connected via a cable 9 to a satellite path 62, in which an energy transmitting coil 63 and an antenna 64 are arranged. By means of the energy transmitting coil 63, electrical energy is fed into the energy receiving coil 60 by means of a radio-frequency signal, such that the microelectrode array 1 is wirelessly supplied with the electrical energy required for its operation. Bidirectional data communication between the electronic control device 10 and the microelectrode array 1 takes place via the antennas 61, 63.

The invention claimed is:

1. A method for obtaining brain wave data using a microelectrode array having a multiplicity of electrodes configured to electrically measure brain waves and an optical stimulation unit configured to stimulate brain regions with optical signals, wherein the optical stimulation unit and the multiplicity of electrodes are integrated onto a common substrate, the stimulation unit having at least one electrical light source arranged according to a fixed, predefined scheme relative to the electrodes and distributed over the areal extent of the substrate, the method comprising:
   stimulating, via optical signals produced by the at least one electrical light source, neurons of the brain;
   recording, via the electrodes, a response of the neurons to the stimulation;
   unambiguously assigning, in a one-to-one manner, the recorded response to individual optical stimulation signals provided by the at least one electrical light source; and
   determining an unambiguous correlation between the optical stimulation signals and resulting brain waves measured by the electrodes.

2. The method as claimed in claim 1 further comprising using electrodes arranged in a manner distributed over the areal extent of a filmlike, thin substrate to electrically measure brain waves, the distribution comprising at least one of a distribution on the surface of the substrate or a distribution in the substrate.

3. The method as claimed in claim 1, wherein stimulating the neurons of the brain includes using a multiplicity of electrical light sources arranged in a manner distributed over the areal extent of a filmlike, thin substrate, the distribution comprising at least one of a distribution on the surface of the substrate or a distribution in the substrate.

4. The method as claimed in claim 1 further comprising using a substrate comprising a transparent film material to electrically measure brain waves.

5. The method as claimed in claim 1, wherein stimulating the neurons of the brain includes using electrically conductive structures formed on a surface of the substrate or in the substrate, said electrically conductive structures forming electrodes, electrical connection lines to the electrodes and/or electrical connection lines to the electrical light source or the electrical light sources.

6. The method as claimed in claim 1 further comprising bringing a sensor side of the microelectrode array into contact with the brain surface of a living being to be examined, wherein the sensor side comprises at least one electrical light source arranged at a greater distance from the sensor side than the electrodes.

7. The method as claimed in claim 1, wherein using the microelectrode array having at least one electrical light source comprises using a microelectrode array having a plurality of electrical light sources, and at least one of the plurality of electrical light sources is arranged as an SMD component, as a die or as a thin-film element on the substrate or within the substrate.

8. The method as claimed in claim 1, wherein stimulating the neurons of the brain includes using a plurality of electrical light sources, with at least one of the electrical light sources being embodied as a light emitting diode.

9. The method as claimed in claim 1 further comprising bringing a sensor side of the microelectrode array into contact with the brain of a living being to be examined, wherein the sensor side is electrically and biologically passivated.

10. The method as claimed in claim 1 further comprising bringing a sensor side of the microelectrode array into contact with the brain surface of a living being to be examined, wherein at least one of the electrodes is integrated into the material of the substrate with the substrate, on the sensor side, having openings leading to the integrated electrodes.

11. The method as claimed in claim 1 further comprising using at least one electrode embodied as an ECoG electrode to electrically measure the brain waves.

12. The method as claimed in claim 1 further comprising stimulating brain regions with electrical signals using at least one stimulation electrode.

13. The method as claimed in claim 12 further comprising using at least one of the electrodes for electrically measuring brain waves and simultaneously for stimulating brain regions with electrical signals.

14. The method as claimed in claim 1, wherein stimulating the neurons of the brain includes using at least one further electrical and/or electronic component arranged in relative proximity to the at least one electrical light source.

15. The method as claimed in claim 14 wherein stimulating the neurons of the brain includes using at least one further electrical and/or electronic sensor component which outputs an electrical sensor signal, the at least one further electrical and/or electronic sensor component arranged in relative proximity to the at least one electrical light source in such a way that at least one physical variable influenced by the at least one electrical light source is detectable by the respective at least one further sensor component.

16. The method as claimed in claim 15 further comprising assigning at least one sensor component of the at least one electrical light source to the respective light source, and assigning an electrical sensor signal output by the at least one sensor component to the influenced physical variable of a specific at least one light source.

17. The method as claimed in claim 15 further comprising using a temperature sensor as the at least one sensor component.

18. The method as claimed in claim 15 further comprising using a light-sensitive sensor as the at least one sensor component.

* * * * *